United States Patent [19]

Koh et al.

[11] Patent Number: 5,667,999

[45] Date of Patent: Sep. 16, 1997

[54] PROCESS FOR PREPARING A FERMENTATION PRODUCT HAVING SOD ACTIVITY USING A MICROORGANISM AND A BEVERAGE CONTAINING THE SAME

[75] Inventors: Kwang Jin Koh; Byoung Youl Jang; Jin Hee Lee; Kang Pyo Lee; Un Young Kong, all of Seoul, Rep. of Korea

[73] Assignee: Cheil Jedang Corporation, Seoul, Rep. of Korea

[21] Appl. No.: 675,484

[22] Filed: Jul. 3, 1996

[30] Foreign Application Priority Data

Apr. 23, 1996 [KR] Rep. of Korea ............ 9612424

[51] Int. Cl.$^6$ .................... A61K 38/44; C12N 9/02
[52] U.S. Cl. .................... 435/189; 424/94.4; 426/7; 426/61; 435/71.2; 435/170; 435/252.5
[58] Field of Search ............ 424/94.4; 435/170, 435/189, 71.2, 252.5; 426/7, 61

[56] References Cited

FOREIGN PATENT DOCUMENTS 2-100640  4/1990  Japan .
6-9474    2/1994  Japan .

OTHER PUBLICATIONS

J.M. McCord et al., "Superoxide Dismutase, An Enzymic Function for Erythrocuprein (hemocuprein)*", *The Journal of Biological Chemistry*, vol. 244, No. 22, Nov. 25, 1969 (pp. 6049–6055).

Statement of Relevancy [Japanese Laid–Open Publication No. (Hei) 2–100640 and Japanese Patent Publication No. (Hei) 6–9474].

*Primary Examiner*—Herbert J. Lilling
*Attorney, Agent, or Firm*—Burns, Doane, Swecker & Mathis, L.L.P.

[57] ABSTRACT

A process for preparing a fermentation product having superoxide dismutase (SOD) activity, which can reduce blood alcohol level and eliminate foul alcohol breath using a novel microorganism of the Bacillus species, and a beverage containing the fermentation product.

3 Claims, No Drawings

PROCESS FOR PREPARING A FERMENTATION PRODUCT HAVING SOD ACTIVITY USING A MICROORGANISM AND A BEVERAGE CONTAINING THE SAME

BACKGROUND OF THE INVENTION

1. Field Of The Invention

The present invention relates to a process for preparing a fermentation product having superoxide dismutase (hereinafter, referred to "SOD") activity using a novel microorganism of the Bacillus species and a beverage containing the fermentation product. The fermentation product can effectively reduce the blood alcohol level, and at the same time eliminate foul alcohol breath.

2. Description Of The Prior Art

SOD is an enzyme that exists in the human body. It protects against harm caused by activated oxygen by convening superoxide to $H_2O$. However, the SOD has a high molecular weight, and cannot be absorbed into the human body by oral administration. In addition, it is difficult to maintain its in vivo activity when it is administered even by injection. In contrast, a SOD-like material which exists in nature is well absorbed into the body, and has an in vivo function. Thus, the material is effective in eliminating alcohol free radicals which are generated as a consequence of ethanol oxidation after drinking. It has a low molecular weight between 200 to 400. An example of the SOD-like material includes flavonoids, polyphenols, tannin, carotene, and so forth. The material is mainly contained in embryo buds of cereals, rice bran, soybean, sesame, etc.

Processes for preparing fermentation products are disclosed in Japanese Unexamined Patent Publication No. (Hei) 2-100640 and Japanese Examined Patent Publication No. (Hei) 6-9474. The former discloses a process for producing boiled rice additives which comprises fermenting a microorganism in an alkaline medium (pH 9–11) containing rice bran, soybean powders and water, filtering the fermented liquor, adding a saponin into the resulting filtrate, and adjusting the pH of the mixture with citric acid to 2.5–3.5. The latter discloses a process for preparing a fermentation product which can reduce blood alcohol level and eliminate foul alcohol breath by inoculating Bacillus natto or Bacillus subtilis into an alkaline medium (pH 7.5–10.0) containing rice bran, soybeans, a carbon source and water, and cultivating the inoculate by aerial stirring.

However, the above prior art processes have drawbacks that both require the fermentation in an alkaline medium and a pH controlling step in purifying the fermented liquor, which consume much time and increase costs.

SUMMARY OF THE INVENTION

The object of the present invention is, therefore, to provide a new process capable of efficiently preparing a fermentation product having SOD activity which can reduce blood alcohol level and eliminate foul alcohol breath by using the novel Bacillus subtilis strain CFC-1234 (KCCM-10082).

Another object of the present invention is to provide a beverage composition comprising:

| | |
|---|---|
| The fermentation product of the present invention | 1–10 wt. % |
| Bread yeast extract (glutathione content 1–10%) | 0.1–0.2 wt % |
| Taurine | 0.01–2 wt % |
| Ganoderma lucidum extract | 0.1–1.0 wt % |
| Fructose | 1–15 wt % |
| Citric acid | 0.1–0.5 wt % |
| Vitamin $B_2$ | 0.001–0.1 wt % |
| Other (acid, vitamins, sugars and flavoring) | trace amount |
| Water | remainder |

These and other objects of the invention can be achieved by a process for preparing fermentation product having SOD activity which can reduce blood alcohol level and eliminate foul alcohol breath using a novel Bacillus subtilis strain CFC-1234 (KCCM-10082), and a beverage composition containing the fermentation product.

Further objects and advantages of the invention will become apparent in the remainder of the specification.

DETAILED DESCRIPTION OF THE INVENTION

We, the inventors of the present invention, have separated various Bacillus genus strains from a conventional bean-paste prepared with ground fermented soybeans and studied them. As a result, we have discovered that a strain CFC-1234 (KCCM-10082) can produce a fermentation product having high SOD activity and can also grow at neutral pH without a separate pH controlling step, and that the produced fermentation product endows an enhanced alcohol resistance compared with conventional products. We have completed the present invention based on this finding.

According to the first aspect of the present invention, a process for preparing a fermentation product having SOD activity which can reduce blood alcohol level and eliminate foul alcohol breath is provided. The process comprises inoculating Bacillus subtills strains CFC-1234 (KCCM-10082) into a medium having a suitable pH range, cultivating the inoculates with agitation and aeration; and recovering the fermentation product having the SOD activity from the fermented mixtures thus produced.

In the description throughout the present specification, the terms "fermentation product" or "fermentation product having SOD activity" refers to fermented products containing the SOD-like materials which have the same function as the SOD enzyme or the function similar to the SOD enzyme. Therefore, it would be understood to the skilled in the art that the term "fermentation product" according to the present invention contains those SOD-like materials.

The term "neutral pH" in the present invention is conveniently defined to mean an appropriate pH range between 5.5 and 7.4, although pH 5.5 is generally regarded to be acidic. Thus, the term "neutral pH" in the present invention should be understood to encompass the pH range between 5.5 and 7.4.

When alcohol, i.e., ethanol is taken into the human body, it is oxidized to give acetaldehyde. In the course of the metabolism of ethanol and acetaldehyde, the ratio of coenzymes, NAD/NADH which are responsible for alcohol decomposition is reduced to destroy in vivo metabolism valance, and harm occurs from the oxygen radicals generated during the ethanol oxidation. Among these, free radicals which are produced from the ethanol oxidative decomposition are recognized as an important factor for liver failure caused by drinking. Thus, effective removal of such alcohol free radicals is required.

The formation of these free radicals by ethanol is believed to occur, first, in the respiratory chain by the mitochondria, second in a microsome by cytochrome P450, and finally in the cytoplasm by a xanthine oxidase which is induced by ethanol.

The method of preparing the fermentation product according to the present invention is described, in detail, below.

To remove the oxygen radicals, the present inventors have extracted a fermentation product having an SOD (exogenous oxidant) activity from natural defatted rice brans, etc. by a conventional fermentation process. The activity of the fermentation product depends mainly on the properties of the microorganism strains involved. When one carries out the microbial fermentation according to the present invention, the SOD-like materials existing in rice brans are effectively extracted by an enzymatic function of the microorganisms to result in an elevation of the activity of the fermentation product. This fermentation process is more efficient than other extraction methods in an aspect of the extraction ability of the effective ingredients.

The extraction of the fermentation product having SOD activity according to the present invention is performed by a fermentation using strain CFC-1234 of *Bacillus subtilis*. The strain can produce a fermentation product having high SOD activity, which was isolated from conventional Korean bean-paste called "Chong-Kuk-Jang" prepared from ground fermented soybeans. This paste is produced by natural fermentation, wherein washed soybeans are immersed in water for 10-20 hours, the soybeans are boiled or steamed for 5-6 hours to the extent that the tissues of the soybeans are destroyed, and it is poured into a bowl and allowed to stand for 2-3 days in a warm room at 40° C., then microorganisms are naturally inoculated to produce fermentation. The resulting fermentation product is mixed with an appropriate amount of salts, seasoning and spice, and is subject to pulverization and aging at 30° C. or below in a jar. The strain can be obtained by the following procedures: First, a number of various bean-pastes prepared from ground fermented soybeans are added into a medium having neutral pH, and the mixtures are cultivated with shaking for about 20 hours at 30° C. The neutral medium contains 1.0% water soluble starch by weight, 0.5% yeast extract by weight, 0.5% polypeptone by weight, 0.1% $Na_2HPO_4$ by weight, and 0.02% $MgSO_4.7H_2O$ by weight (pH 7.0). The culture broths were then streaked on flat media containing 1.5% of bacto-agar by weight besides the above neutral medium composition to separate single colonies. After the single colonies thus separated were inoculated into a neutral titer medium, and cultivated with shaking for 48 hours at 30° C., the strain showing the highest titer of SOD activity in the media was selected. The neutral titer medium is made from a natural raw material, defatted rice bran. The composition of the culture medium comprises 6.0% defatted rice bran by weight, 0.8% soybean peptides by weight, 1.0% phytic acid by weight, 2.0% $Na_2HPO_4$ by weight, 0.5% $(NH_4)_2HPO_4$ by weight, 0.16% $Na_2CO_3$ by weight, and 3.0% of glucose by weight (pH 7.0).

The determination of the SOD activity was carried out by the known McCord and Fridovich method [J. Biol. Chem. Vol. 244, No. 22, pp.6049–6055 (1969)] wherein in xanthine-xanthine oxidase systems, the level that inhibits the reduction of cytochrome C by $O_2.^-$ is determined by SOD activity. The amount of SOD required to inhibit the rate of reduction of cytochrome C by 50% is defined as 1 unit of activity.

According to another aspect of the present invention, a beverage composition is provided, having the following components:

| | |
|---|---|
| The fermentation product of the present invention | 1–10 wt % |
| Bread yeast extract (glutathione content 1–10%) | 0.1–2 wt % |
| Taurine | 0.01–2 wt % |
| *Ganoderma lucidum* extract | 0.1–1.0 wt % |
| Fructose | 1–15 wt % |
| Citric acid | 0.1–0.5 wt % |
| Vitamin $B_2$ | 0.001–0.1 wt % |
| Other (acids, vitamins, sugars and flavoring) | trace amount |
| Water | remainder |

Preferably, a beverage composition for endowing a subject with an alcohol resistance effect contains 1–10 wt % of the fermentation product produced according to the present invention. When the composition contains one wt % or less of the fermentation product, it is difficult to obtain enough alcohol resistance effect. When the composition contains 10 wt % or more of the fermentation product, it is undesirable since it may cause the taste or flavor of the product deteriorated.

DESCRIPTION OF THE PREFERRED EMBODIMENTS

The present invention will be illustrated in greater detail by way of the following examples. The examples are presented for illustrative purpose only and should not be construed as limiting the invention, which is properly delineated in the claims.

EXAMPLE 1

To obtain a *Bacillus subtilis* strain having a high SOD titer, a single colony was isolated from the conventional bean-pastes prepared from ground fermented soybeans as described hereinabove, and subjected to the first selection (See Table 1). The colony was cultivated in the said neutral liter media, and the SOD activity of the fermentation product was measured by the above McCord and Fridovich method. A strain showing the greatest increase in SOD activity was selected by comparing the fermentation product before fermentation. As can be seen from Table 1, the second colony showed about 80 Units/g of SOD activity which is about 7 times the SOD titer of the media composition before fermentation, was finally selected, and named *Bacillus subtilis* strain CFC-1234. The strain CFC-1234 was deposited on Apr. 17, 1996 in the KCCM (Korean Culture Center of Microorganism, Department of Food Engineering, College of Eng. Yonsei University, Sodaemun-gu, Seoul 120–749, Republic of Korea) which is one of the international depositories recognized under the Budapest Treaty and received the deposit number KCCM 10082. This deposit was made according to all of the requirements of the Budapest Treaty.

TABLE 1

| Selection of strains showing SOD activity | | |
|---|---|---|
| Colony number | SOD activity after fermentation | Note |
| 1 | 20 | *The activity before fermentation was 11 Unit/g |
| 2 | 80 | |
| 3 | 30 | |
| 4 | 50 | |
| 5 | 18 | |

TABLE 1-continued

Selection of strains showing SOD activity

| Colony number | SOD activity after fermentation | Note |
|---|---|---|
| 6 | 17 | |
| 7 | 12 | |
| 8 | 11 | |
| 9 | 11 | |
| 10 | 12 | |

EXAMPLE 2

To elucidate an appropriate pH range for cultivating the strain (colony 2) isolated as in the Example 1, the strain was cultivated in various media in which the pH was preadjusted to 4.5, 5.0, 5.5, 6.0, 7.0, 7.5, and 8.0 respectively with a buffer solution, for 20 hours at 30° C. under vigorous agitating at 200 r.p.m. The growth media contained 0.3% beef extract by weight and 0.5% peptone by weight. The growth of cells was monitored by determining absorbance at 600 nm. The results are set forth in Table 2.

TABLE 2

Growth of Bacillus subtilis CFC-1234 strain according to various pH conditions

| Absorbance (600 nm) | pH | | | | | | |
|---|---|---|---|---|---|---|---|
| | 4.5 | 5.0 | 5.5 | 6.0 | 7.0 | 7.5 | 8.0 |
| Before culture | 0.01 | 0.01 | 0.01 | 0.01 | 0.01 | 0.01 | 0.01 |
| After culture for 20 hours | 0.01 | 0.40 | 1.00 | 1.50 | 2.50 | 0.55 | 0.01 |

As can be seen from Table 2, the strain isolated by the present invention showed a rapid growth in the media having a neutral pH between 5.5 and 7.5. Cell growth hardly occurred in the media having other pH values than the above range. Thus, it was confirmed that the fermentation of this strain should be carried out in a medium having neutral pH (5.5–7.4).

EXAMPLE 3

The strain (colony 2) isolated as in Example 1 was seed cultivated in a liquid nutrient growth media containing 0.3% beef extract by weight and 0.5% peptone by weight for 20 hours at 30° C. with vigorous agitating at 200 r.p.m. 2 ml of the seed cultures was inoculated into a fermenter containing a neutral media comprising 6.0% defatted rice bran by weight, 0.8% soybean peptide by weight, 1.0% phytic acid by weight, 2.0% $Na_2HPO_4$ by weight, 0.5% $(NH_4)_2HPO_4$ by weight, 0.16% $Na_2CO_3$ by weight, and 3.0% glucose by weight (pH 7.0), each of which temperature was pre-set to 25°, 30°, 35°, 40° and 45° C., respectively, and cultivated for 18 to 22 hours. The volume of the medium in the fermenter was 2.5 l, the agitating rate was 600–800 r.p.m., and the aeration rate was 1.0 vvm(volume/volume minute). Additional pH adjusting was not carried out. The growth of the cells has proportionally correlated with the SOD activity of the fermentation product. After completion of the fermentation, the temperature range within which the cells can most vigorously grow was determined by measuring the SOD activity of the product. The results are set forth in Table 3.

TABLE 3

Growth effect according to culture temperature

| | Temperature (°C.) | | | | |
|---|---|---|---|---|---|
| | 25 | 30 | 35 | 40 | 45 |
| SOD Activity (Unit/g) | 40 | 87 | 90 | 85 | 52 |

As can be seen from Table, the temperature range for optimum cell growth falls between 30° and 40° C. Above this temperature range, the cell growth declined, and the SOD activity of the product was low.

EXAMPLE 4

The fermentation product obtained from Example 3 was subjected to heat treatment for 30 minutes at 80° C., and cooled until precipitates were formed. The precipitates were filtered using a pressure filter employing a perlite as a filtering aid. The filtrates were then reacted with 1% of an activated carbon for an hour. The reactants were then filtered with the above pressure filter to provide decolorized and deodorized filtrates. The filtrates were finally ultrafiltered with a separating membrane made of a cellulose through which material whose molecular weight is below 10,000 can pass under the condition of 10–20 psi of intermembrane pressure, and volumetric concentration rate of 5.0 to give fermentation products from which SOD-like materials were then collected and purified.

EXAMPLE 5

A beverage composition was prepared from the fermented extracts prepared through Examples 3 and 4 according to Table 4 below. For a comparison, a conventional beverage composition was prepared from a fermentation product similar to the beverage composition in Table 4. The conventional fermentation product was prepared by the process described in the Japanese Examined Patent Publication No. (Hei) 6-9474.

TABLE 4

The composition of beverage

| Composition | Ratio (% by weight) |
|---|---|
| The fermentation product of the present invention | 5.0 |
| Bread yeast extract (glutathione content 1–10%) | 1.0 |
| Taurine | 0.8 |
| Ganoderma lucidum extract | 0.5 |
| Fructose | 10 |
| Citric acid | 0.3 |
| Vitamin $B_2$ | 0.001 |
| Vitamin C | 0.1 |
| Flavoring | trace amount |
| Purified water | remainder |

Thirty healthy persons of ages 20 to 40 years, none of whom had an abnormality in alcohol metabolism, were selected and divided to three groups. Each of the first group was provided with an alcohol beverage only. Each of the second group was provided with 75 ml of the conventional beverage product and the third group, with 75 ml of the beverage composition according to the present invention 10 minutes before drinking. After drinking, foul alcohol breath was measured using an alcohol detector at an interval of every 30 minutes. The results are set forth in Table 5. The numbers for the alcohol level represents an average ppm value.

TABLE 5

Alcohol level after drinking

| Time (hour) | Alcohol level | | |
|---|---|---|---|
| | Drinking only | Drinking after taking conventional beverage | Drinking after taking beverage of the invention |
| 0 | 0.0000 | 0.0000 | 0.0000 |
| 0.5 | 0.0375 | 0.0252 | 0.0121 |
| 1.0 | 0.0297 | 0.0200 | 0.0087 |
| 1.5 | 0.0185 | 0.0145 | 0.0056 |
| 2.0 | 0.0124 | 0.0098 | 0.0038 |
| 3.0 | 0.0040 | 0.0033 | 0.0021 |

As can be seen from Table 5, the beverage composition according to the present invention provided a superior elimination of blood alcohol and foul alcohol breath as compared with the conventional beverage composition.

What is claimed is:

1. A process for preparing fermentation product having SOD activity and capable of reducing blood alcohol level and eliminating foul alcohol breath, which comprises inoculating *Bacillus subtilis* strains CFC-1234 CKCCM-10082) into a medium having a suitable pH range, cultivating the inoculates with agitation and aeration; and recovering the fermentation product having the SOD activity from the fermented mixtures thus produced.

2. The process according to claim 1, wherein the suitable pH range is between 5.5 and 7.4.

3. The process according to claim 1, wherein the cultivation is carried out at temperature between 30° and 40° C.

* * * * *